United States Patent [19]

Sliski

[11] Patent Number: 5,511,107
[45] Date of Patent: Apr. 23, 1996

[54] X-RAY PHANTOM APPARATUS

[75] Inventor: Alan P. Sliski, Lincoln, Mass.

[73] Assignee: Photoelectron Corporation, Waltham, Mass.

[21] Appl. No.: 286,757

[22] Filed: Aug. 5, 1994

[51] Int. Cl.⁶ ................................................. G01D 18/08
[52] U.S. Cl. ........................... 378/207; 378/174; 378/64
[58] Field of Search ................................. 378/207, 204, 378/167, 174, 64, 65, 18

[56] References Cited

U.S. PATENT DOCUMENTS

| | | |
|---|---|---|
| Re. 31,847 | 3/1985 | Luckey . |
| 3,010,223 | 11/1961 | Alderson ........................... 378/207 X |
| 3,031,575 | 4/1962 | Gevantman et al. . |
| 3,582,219 | 6/1971 | Pfeifer . |
| 3,867,638 | 2/1975 | Golden ............................... 378/207 X |
| 4,717,258 | 1/1988 | Sutton . |
| 4,900,930 | 2/1990 | Takiguchi et al. . |
| 5,021,978 | 6/1991 | Stone et al. . |
| 5,255,069 | 10/1993 | Duarte . |

FOREIGN PATENT DOCUMENTS

| | | | |
|---|---|---|---|
| 1152442 | 5/1969 | United Kingdom ................... | 378/207 |

OTHER PUBLICATIONS

Medical Physics, vol. 20, No. 3, May/Jun. 1993, pp. 925–926.

*Primary Examiner*—David P. Porta
*Attorney, Agent, or Firm*—Lappin & Kusmer

[57] ABSTRACT

A system is disclosed for producing images representing radiation dose distributions in order to verify the radiation dose applied to a target area. The system uses a phantom assembly constructed of material that is the radiological equivalent of live tissue. The phantom assembly has slits where radiation sensitive film can be inserted and can include a channel for an insertable radiation generating device. The treatment dose is then applied to the phantom and the radiation sensitive film records the dose. A CCD camera microdensitometer is then used to read the exposed radiation sensitive film. The CCD camera microdensitometer includes a computer system which processes the image to remove artifacts and generates isodose contours for the radiation treatment applied. In addition, several pieces of radiation sensitive film in different planes can be exposed and processed in order to produce images representing the radiation dose distribution in three dimensions.

19 Claims, 10 Drawing Sheets

X-RAY PHANTOM APPARATUS

BACKGROUND OF THE INVENTION

This invention relates to a device for measuring two and three dimensional radiation dose distributions for radiation generating devices. Specifically, the invention relates to a system for recording the dose of radiation delivered to a target area and utilizing one or more recordings to measure radiation dose distributions for the tissue in and adjacent to the target area.

In the field of medicine, radiation is used for diagnostic, therapeutic and palliative treatment of patients. The conventional medical radiation sources used for these treatments include large fixed position machines as well as small, transportable radiation generating probes. The current state of the art treatment systems utilize computers to generate complex treatment plans that are difficult and sometimes impossible to verify using conventional measurement techniques such as ionization chambers which only record the dose at one point in space.

In order to be able to more precisely control the dosage and area of treatment, it is necessary to accurately measure and verify the dose distribution and precisely calibrate the device. This procedure is further complicated by fact that the radiation dosage is affected by the density of the material, the more dense the material the more radiation it will absorb. Therefore it is desirable to model the area to be irradiated in order to verify the proper radiation dose is being applied.

Accordingly, it is an object of this invention to provide an apparatus for measuring the dose distribution for radiation applied to a target area.

It is another object of the invention to provide an apparatus for measuring and recording the dose distribution and generating an image representing the dose distribution of radiation applied to a localized area.

It is another object of the invention to provide an apparatus for measuring and recording the dose distribution and generating an image representing the dose distribution of a miniaturized radiation source in a target area.

It is another object of the invention to provide an apparatus which is capable of measuring and recording the dose distribution and generating an image representing the dose distribution of a predefined radiation treatment plan applied to a medium having known density and radiation absorption characteristics.

It is yet another object of the invention to provide an apparatus which is capable of measuring and recording and generating a three dimensional image representing the dose distribution of radiation applied to a target area.

SUMMARY OF THE INVENTION

The invention relates to a phantom assembly and a microdensitometer. The phantom assembly supports radiation sensitive film in one or more predefined planes and optionally includes a channel for the insertion of a miniaturized radiation source. One preferred radiation sensitive film is radiochromic film. Radiochromic film is a special film used to measure the dose of ionizing radiation delivered to an area and does not require subsequent processing to develop the image. The optical density of the exposed film is proportional to the dose of ionizing radiation received. The radiochromic film is exposed by the radiation source. The radiochromic film is read by the microdensitometer and used to produce isodose contours and a three dimensional representation of the dose distribution.

The phantom assembly is preferably constructed of a tissue equivalent material and formed in substantially the same physical dimensions as the tissue being treated. The phantom assembly includes one or more locations where radiochromic film can be inserted for exposure. Preferably, several pieces of film, each parallel to a common plane but spaced apart at predetermined distances from the target area can be provided. Alternatively, the film can be oriented in three orthogonal planes for measuring the radiation dose applied to the target area in three dimensions.

The microdensitometer consists of a CCD Camera and a uniform light source connected by an optical rail. The CCD Camera is connected to a computer system which processes the image. The optical rail allows the camera to be moved with respect to the light source to change the magnification of the image while maintaining the camera in fixed alignment. The uniform light source includes a light box enclosing multiple light generating elements and a light diffusing element. The wavelength of the light generating elements is matched to the peak absorption wavelength of the exposed radiochromic film. The light generating elements and the diffusing element are designed to provide uniformity of better than 10% in the central area of the light box. The light generating elements are arranged in substantially annular arrays varying with intensity. The annular array with the highest intensity being adjacent the outer edges of the uniform light source. A current control circuit can be provided to adjust the light intensity and optimize the image for the dynamic range of the CCD camera. A photosensing element can also be provided to regulate the light intensity. The computer system acquires images from the camera and processes the images to produce isodose contours.

In order to obtain accurate profiles, the image is processed to compensate for various sources of error and noise. Dark image acquisition errors appear as differences in pixel values for the same level dark image. The system reads a pure black image and stores the dark value for each pixel and uses these dark values to compensate the image. The light image acquisition errors appear as differences in pixel values for the same level light image. They can also be caused by imperfections in the camera lens and non-uniformity of the light source. The system reads a light image and stores the individual light values for each pixel and uses these light values to compensate the image. Frame transfer errors occur when the CCD Camera takes a new image, the camera clocks in a blank image causing some image smearing. The system compensates for this error by first taking a short exposure and subtracting it from the second longer exposure. Scatter compensation error is caused by reflections from the surface of the camera lens, dust on the lens and the surface finish of the lens surfaces. To compensate for scatter error, an opaque object is imaged and a scatter compensation factor is generated as the average pixel value for the area of the opaque object divide by the average pixel value for the entire image. In addition, the system can scan same image of the film several times and take an average of the several scans.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE PREFERRED EMBODIMENTS

The phantom assembly is constructed of a tissue equivalent material and where necessary having the same approximate physical dimensions as the living tissue to be treated with ionizing radiation. The phantom also includes slits or locations where pieces of radiation sensitive film are held. Normally, the slits or locations will be interior to the surface of the phantom, however, the radiation sensitive film can be located adjacent the outer surface of the phantom. As used herein, the locations where radiation sensitive film can be held include locations interior to the phantom as well as adjacent the outer surface. Preferably, the slits are arranged to hold several pieces of film, each parallel to a common plane but spaced apart at predetermined distances. In one alternative embodiment, the slits are arranged to hold the film in three orthogonal planes. In another alternative embodiment, the slits are arranged to hold the film as necessary to record the dose of ionizing radiation for a predetermined area or location with respect to the source of ionizing radiation.

As defined herein, a tissue equivalent material is any material that is the radiological equivalent of living tissue for a given type of radiation. Similarly, SOLID WATER, as used herein, refers to any material that is the radiological equivalent of water for a given type of radiation. SOLID WATER and tissue equivalent materials are available from Radiation Measurements, Inc. of Middleton, Wis.

The radiation sensitive film can be either silver halide based films or radiochromic films. Radiochromic films are preferred because they provide several advantages over silver halide based films. Radiochromic films do not require subsequent processing to develop the image and they are not substantially affected by ambient light. In addition, the peak absorption wavelength of the radiochromic film can be selected based on the radiochromic dye used.

The preferred radiochromic film is GAFchromic film available from ISP Corporation of Wayne, N.J. Preferably, the light source used to image the exposed film is chosen to permit the microdensitometer to discern to a high degree the different levels of dose recorded by film in order to produce a high quality image. The dynamic range and resolution of the image is determined by the wavelength of the light source and the absorption characteristics of the film.

Figure 1:
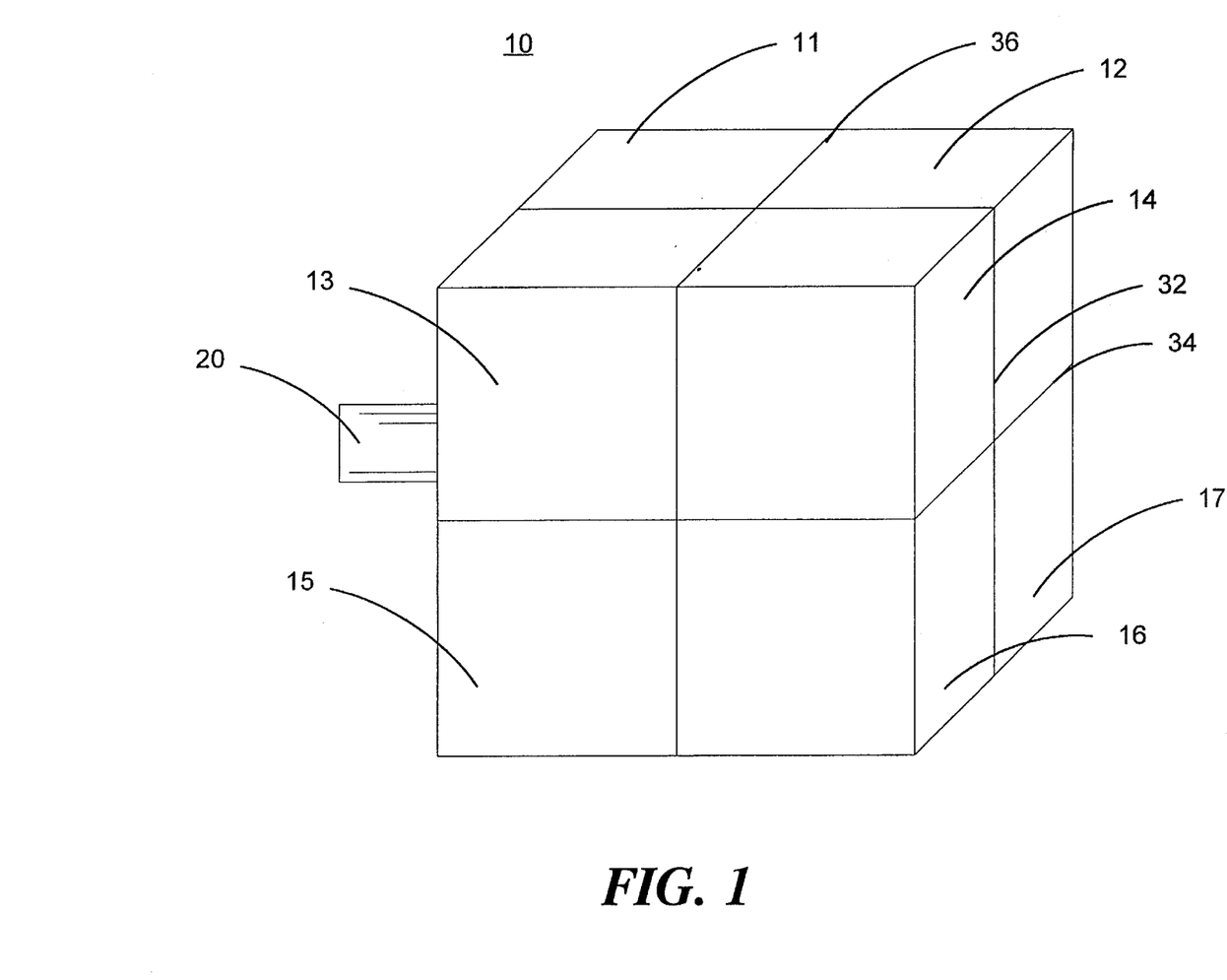
FIG. 1 is a diagrammatic view of a phantom assembly in accordance with the present invention.
Figure 2:
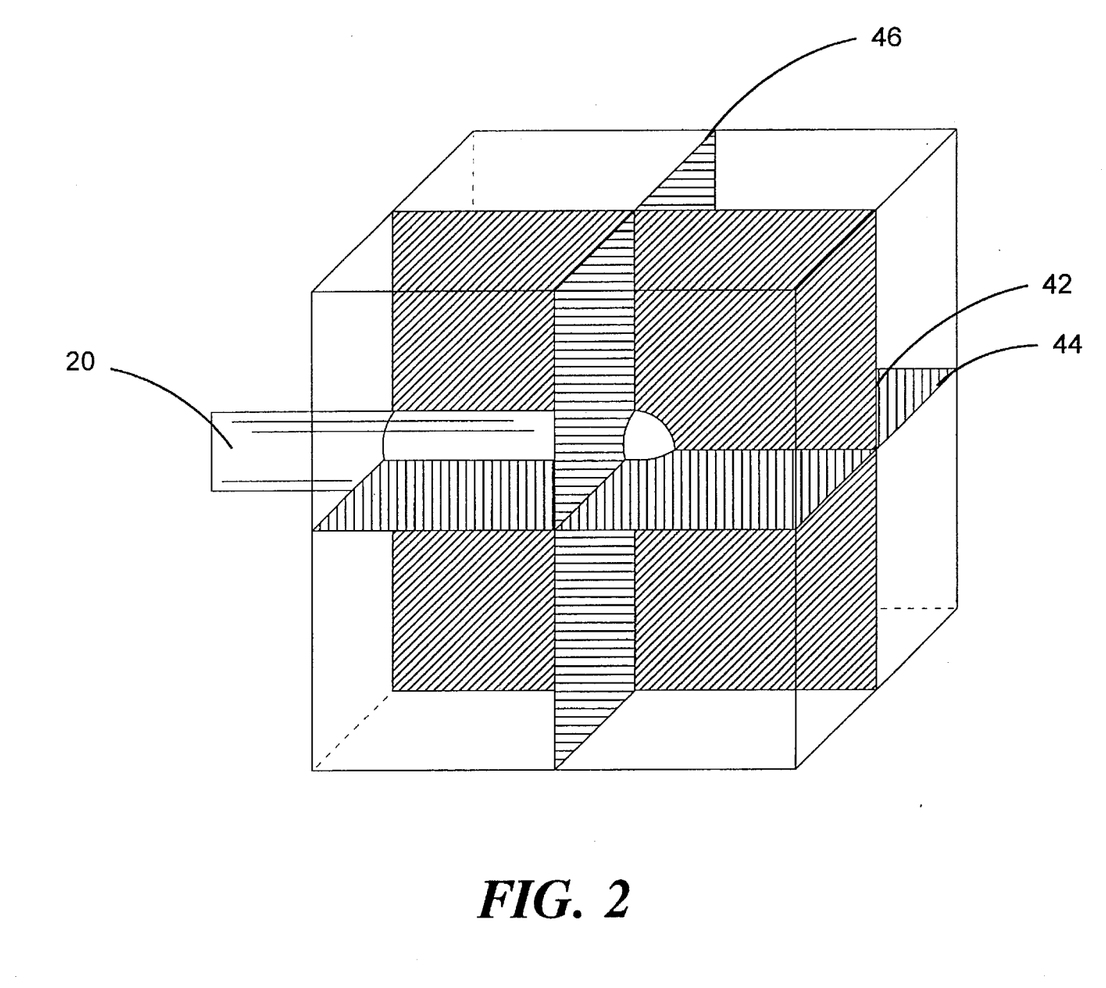
FIG. 2 is a diagrammatic view of the phantom assembly of FIG. 1 showing the radiochromic film locations in accordance with the present invention.

FIGS. 1 and 2 show one embodiment of the phantom assembly in the form of a cube 10. The cube 10 includes 8 smaller sections 11–18 of SOLID WATER or tissue equivalent material wherein the adjacent surfaces of adjacent sections form slits 32, 34, 36 for holding radiochromic film. The cube 10 can also include a channel or opening for the insertion of an X-ray probe 20. An outer shell or frame (not shown) can be provided to hold the sections in position while the film is exposed.

Figure 3:
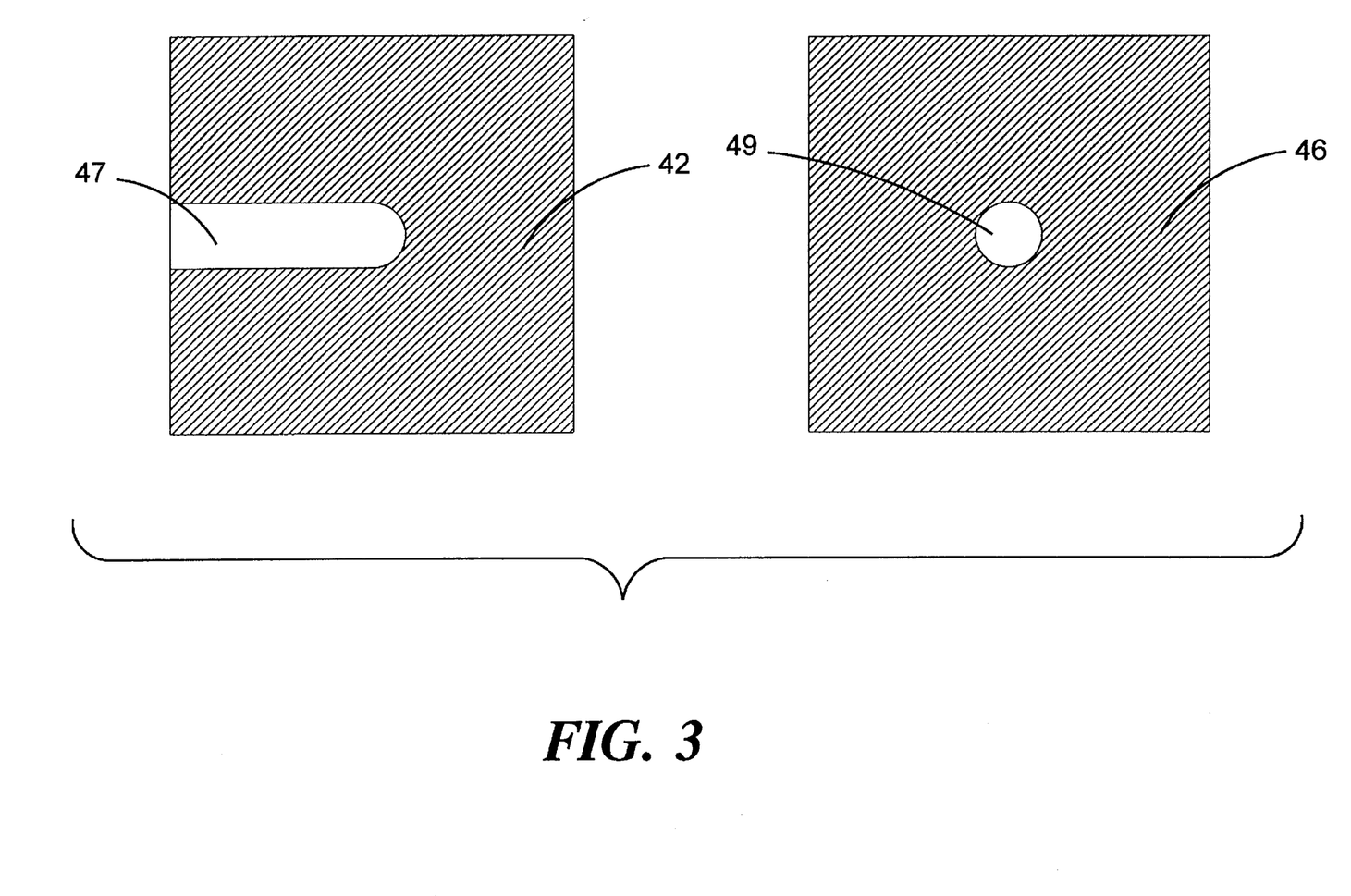
FIG. 3 is a plan view of two shapes of radiochromic film in accordance with the present invention.

As shown in FIG. 3, the radiochromic film can be cut, preferably, into one of two shapes, both rectangular or approximately the dimensions of one surface of the cube. FIG. 3 shows Type A film 42, having a slot 47 extending from one edge toward the center to accommodate the x-ray probe (not shown). FIG. 3 also shows Type B film 46, having a central hole 49 also to accommodate the x-ray probe (not shown). Preferably, the film is laser cut to ensure uniformity.

In this embodiment, one piece of film can be exposed at a time. For example a Type A piece of film 42 is inserted in slit 32 and exposed for a predetermined period of time, then another Type A piece of film 44 is inserted in slit 34 and exposed for the same period of time. Then a Type B piece of film 46 is inserted in slit 36 and exposed for the same period of time. Because the slits 32, 34 and 36 are in three orthogonal planes, the three pieces of film 42, 44, 46 provide images that represent the radiation doses in three dimensions. Utilizing a microdensitometer, these images can be scanned into a computer system and used to produce isodose contours in three dimensions. Alternatively, utilizing conventional image reconstruction techniques, three dimensional dose distributions can be generated.

Figure 4A:
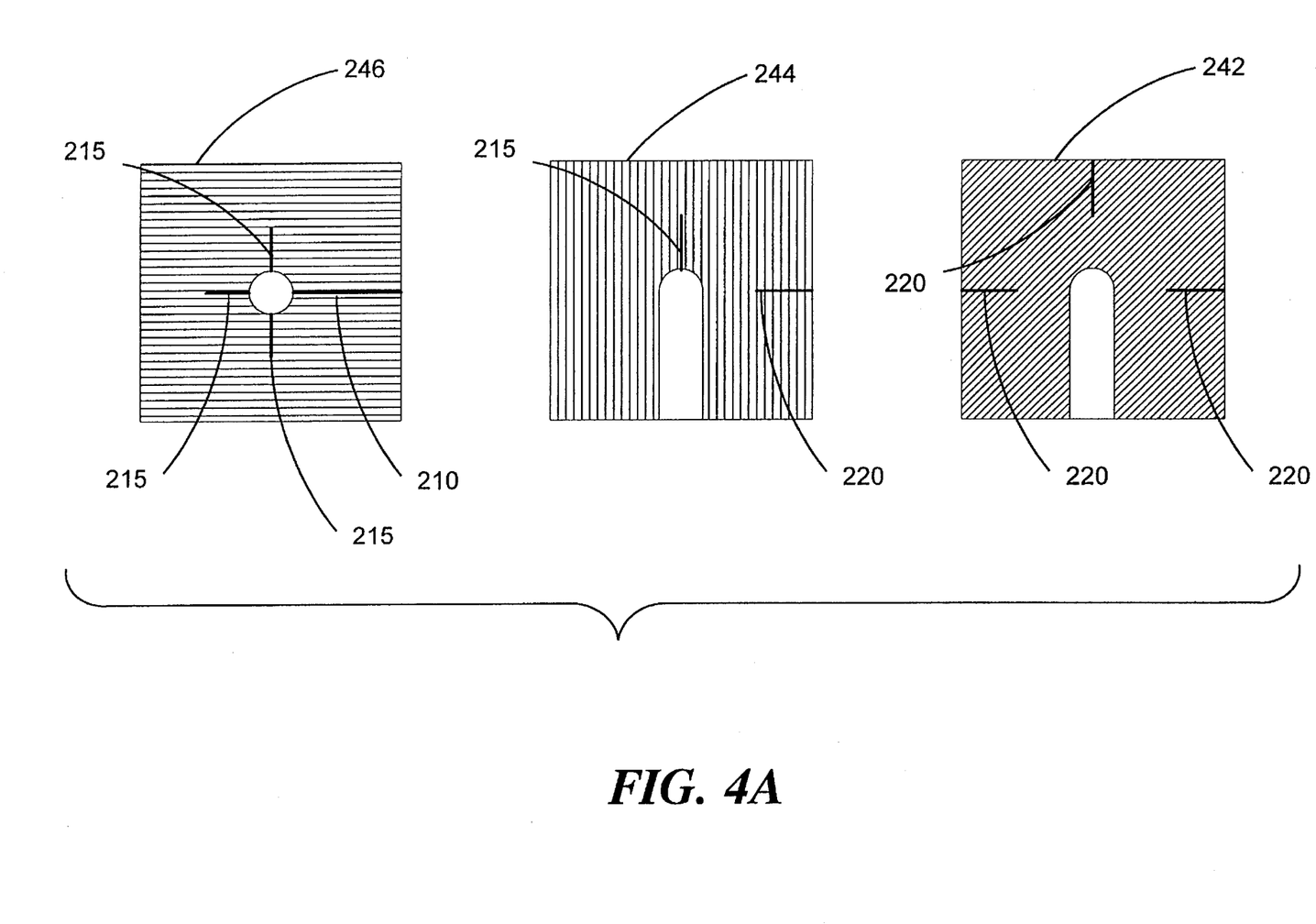
FIG. 4A is a plan view of an alternate set of interlocking shapes of radiochromic film in accordance with present invention.
Figure 4B:
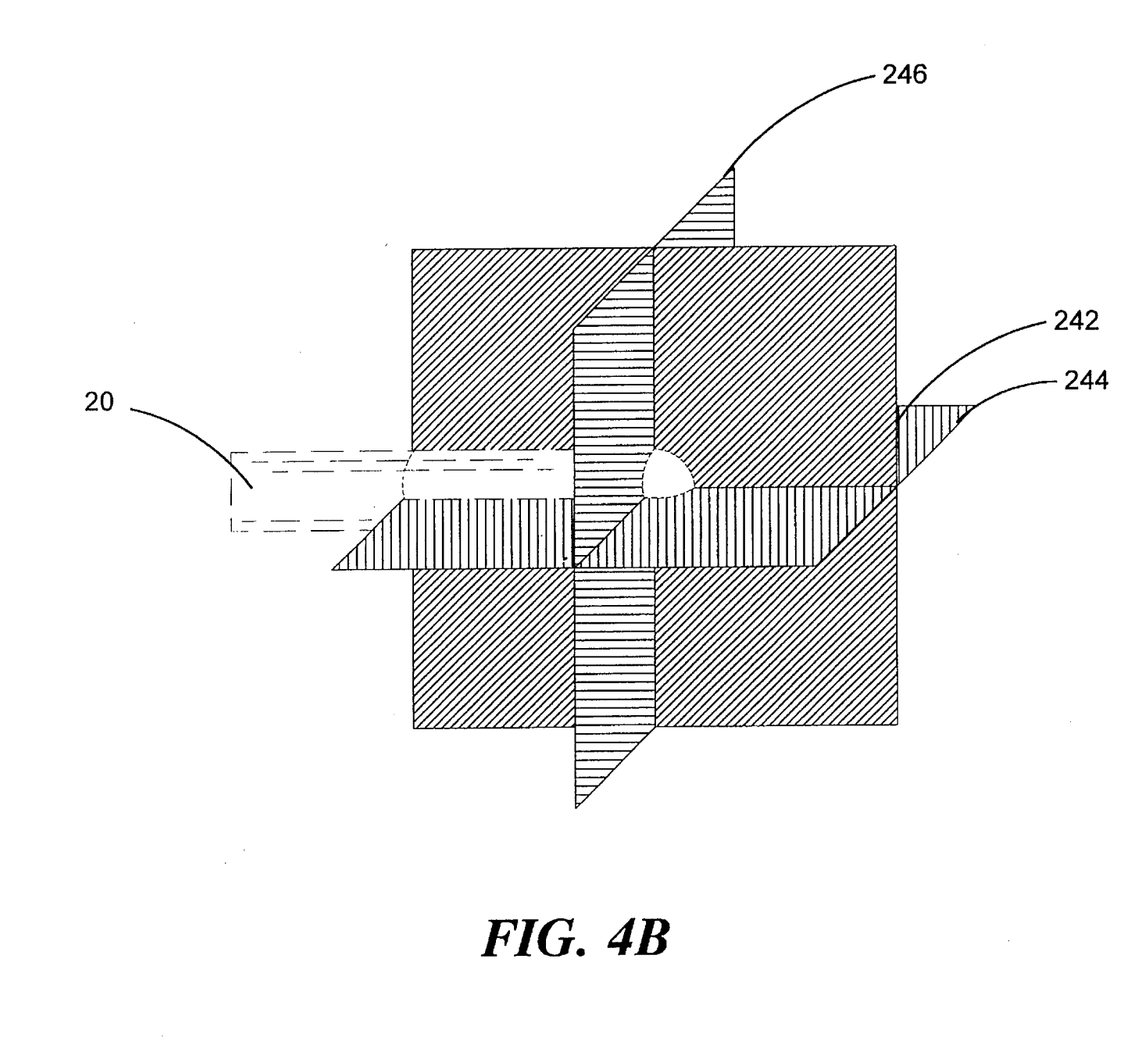
FIG. 4B is an isometric view of the radiochromic film of FIG. 4A in assembled form.

FIGS. 4A and 4B show an alternate embodiment of radiochromic film in accordance with the invention. FIG. 4A shows three pieces of radiochromic film 242, 244, 246 having notches 210, 215, 220 which allow them to be assembled into a self supporting three dimensional assembly. FIG. 4B shows the self supporting three dimensional assembly. In this embodiment, the tissue equivalent material such as that shown in FIG. 1 can be nested around the three dimensional structure. The structure can also include a channel for the insertion of a radiation generating probe 20.

Figure 5:
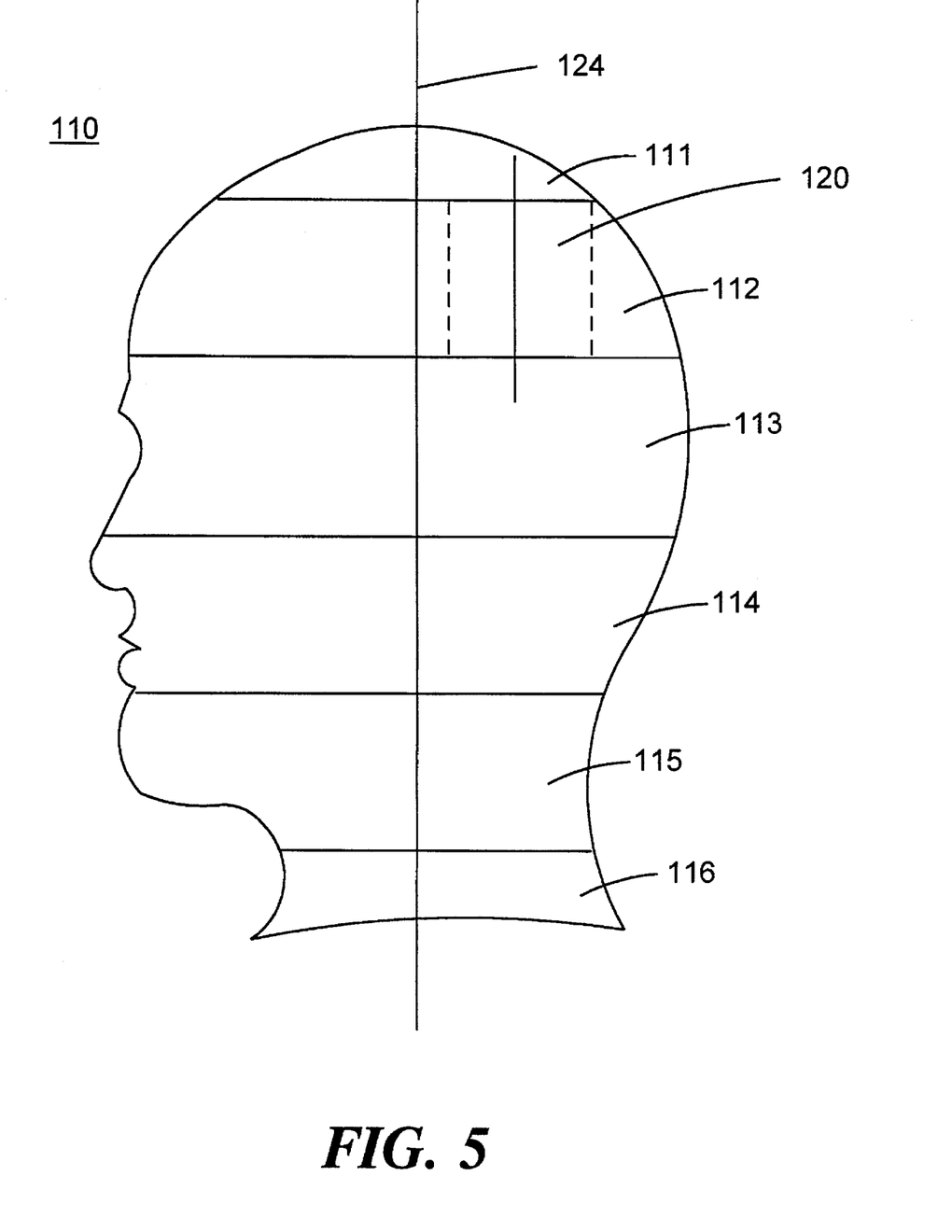
FIG. 5 is a diagrammatic view of an alternative phantom assembly in accordance with the present invention.

FIG. 5 shows an alternative embodiment of invention wherein the physical dimensions of the phantom 110 are same as the part of the body to be treated, in this example, the human head. Preferably, the phantom 110 is constructed of several different types of tissue equivalent material representing the different layers of tissue. In this embodiment, the outer layer can be a soft tissue equivalent layer over a bone equivalent layer surrounding a brain tissue equivalent layer. Alternatively, real bone tissue may be used.

As shown in FIG. 5, the phantom 110 includes a plurality of horizontal slices or sections 111 - 116 transverse to a longitudinal axis 124. The slit between each section can accommodate one or more pieces of radiochromic film. In addition, one or more adjacent sections may include a portion or subsection 120 which is further divided into slices or subsections which can accommodate radiochromic film. In this embodiment, a channel or hole (not shown) can be provided to accommodate an x-ray probe. Alternatively, this embodiment can be used with a conventional external radiation source to measure the dose of radiation applied.

Figure 6:
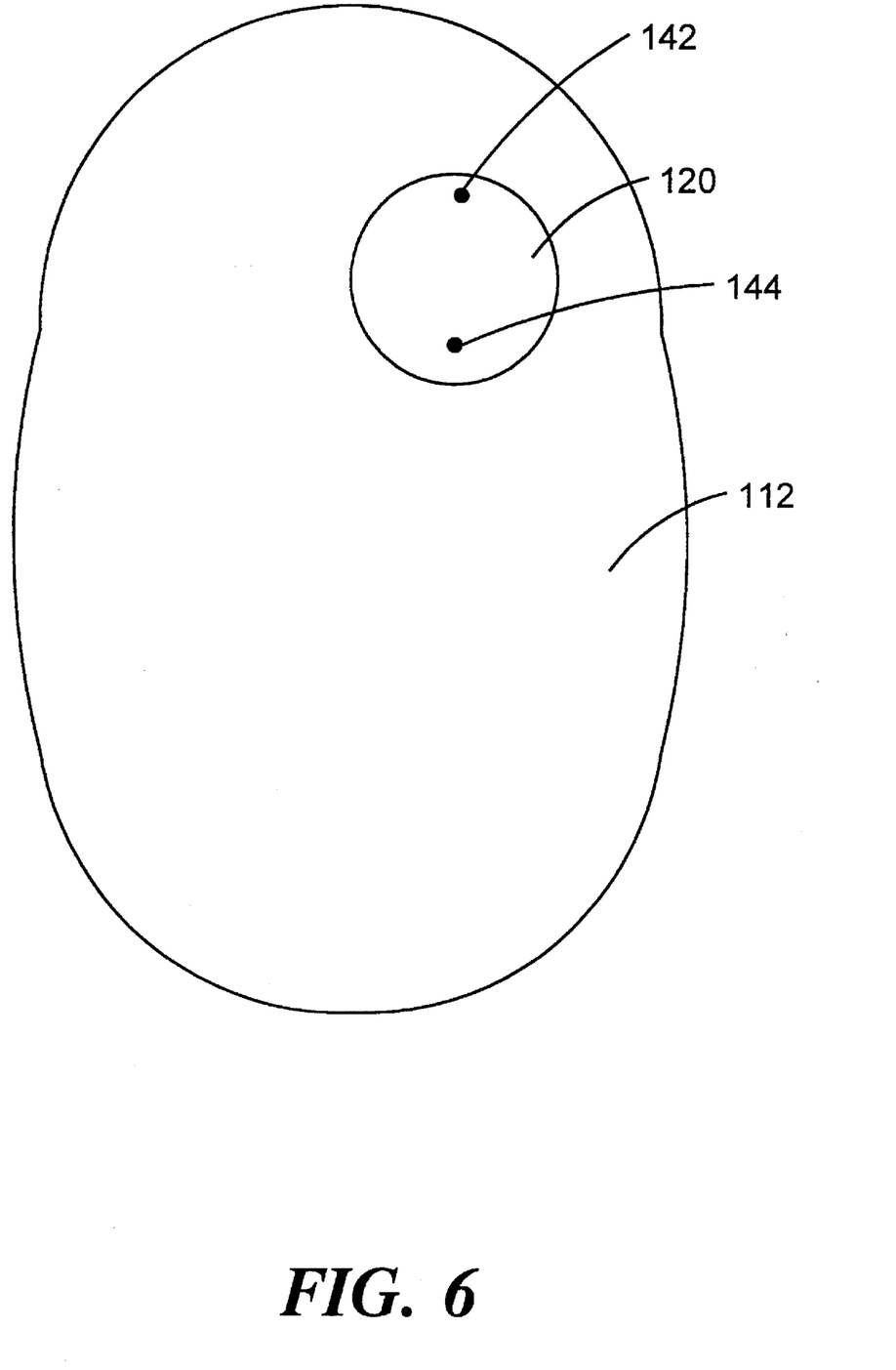
FIG. 6 is a top view of one section of the phantom assembly of FIG. 5 in accordance with the present invention.
Figure 7:
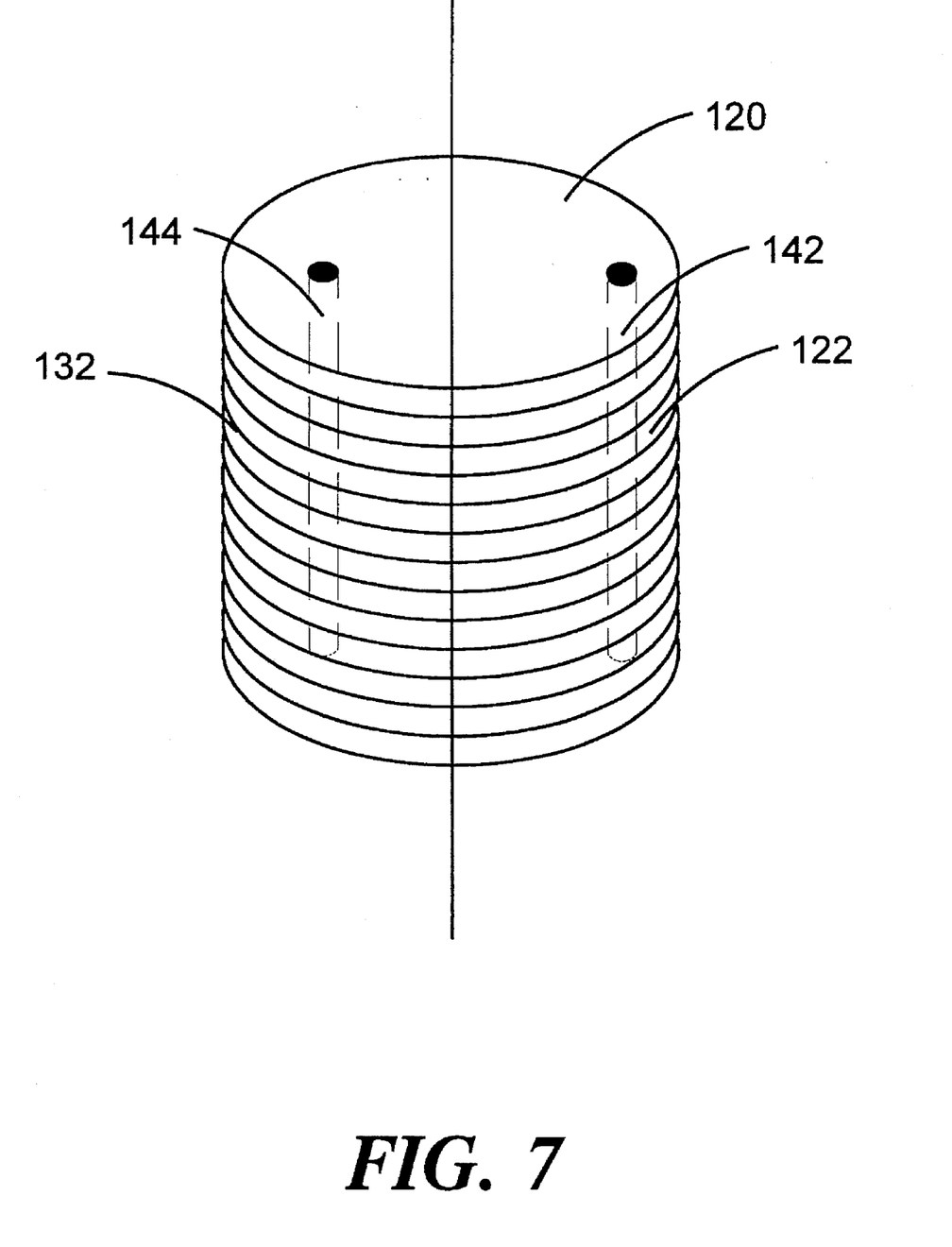
FIG. 7 is a diagrammatic detail view of the subsection assembly shown in FIGS. 5 and 6.

FIG. 6 shows the top view of one slice 112 having a subsection 120 which is further divided into subsection slices. In this embodiment, as shown in FIG. 7, the subsection 120 is a cylindrical portion having a longitudinal axis 126 substantially parallel to the longitudinal axis of the phantom 124. Alternatively, the subsection 120 can be designed to have any cross-sectional shape and to have any orientation whereby the axis of the subsection 126 is at any angle with respect to the axis of the phantom 124 as necessary. The subsection 120 can also include one or more alignment pins 142, 144 to align the subsection slices 132 with respect to one another and to align the subsection with respect to the phantom. The radiochromic film can be provided with holes to accommodate the alignment pins 142, 144 and for determining the orientation of the film after exposure. As shown in the figures, the guide pins 142, 144 are placed in asymmetrical locations with respect to the subsection axis 126 in order to facilitate determining the orientation of the film after exposure. Alternatively, the radiochromic film can be provided with a notch or other indicia (not shown) to facilitate determination of its orientation.

This embodiment is especially well suited for use with external sources of radiation such as Linac machines. These machines typically direct a beam of radiation from outside the body to treat tissue within or beneath bone. In the preferred embodiment, a phantom is constructed of one or more tissue equivalent materials and having the same dimensions as the section of the body to be treated. The phantom is then sectioned around the area to be treated and a subsection is constructed and inserted in the area to be treated. One or more pieces of radiochromic film is inserted between the subsection slices and the subsection is replaced into the phantom. The phantom is reassembled and the radiation treatment is applied. The exposed radiochromic film is analyzed using a microdensitometer to verify that the treatment is appropriate.

Figure 8:
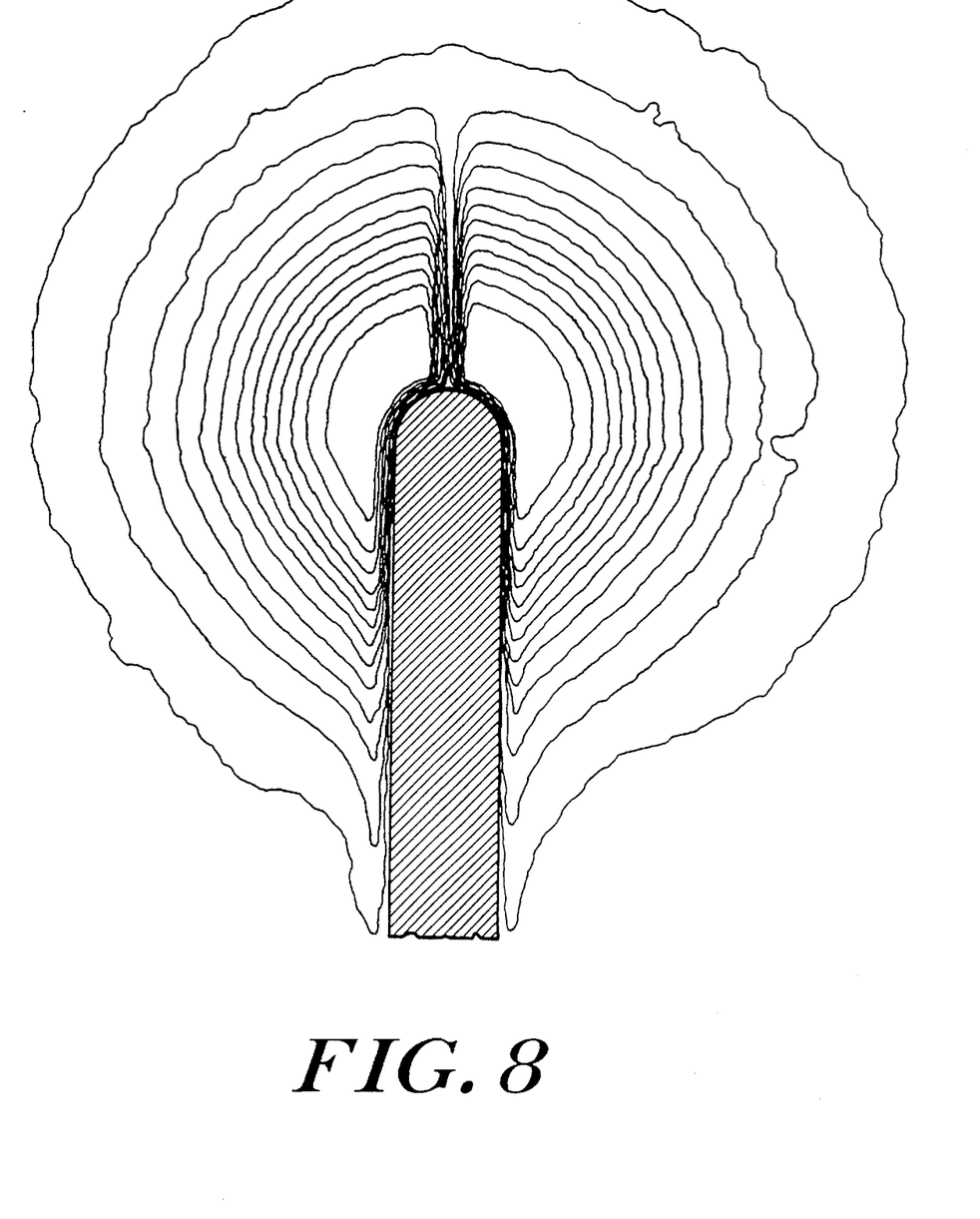
FIG. 8 is a representation of the image produced from radiochromic film.

FIG. 8 shows the resulting image produced with radiochromic film as used in conjunction with the phantom of FIGS. 1–4. The dark lines are isodose contours. The image can also be rendered in color whereby the different colors represent predefined levels of absorbed radiation. Several such images from different planes can be combined using conventional computed tomography techniques to produce a three dimensional representation of the radiation dose distribution.

Figure 5A:
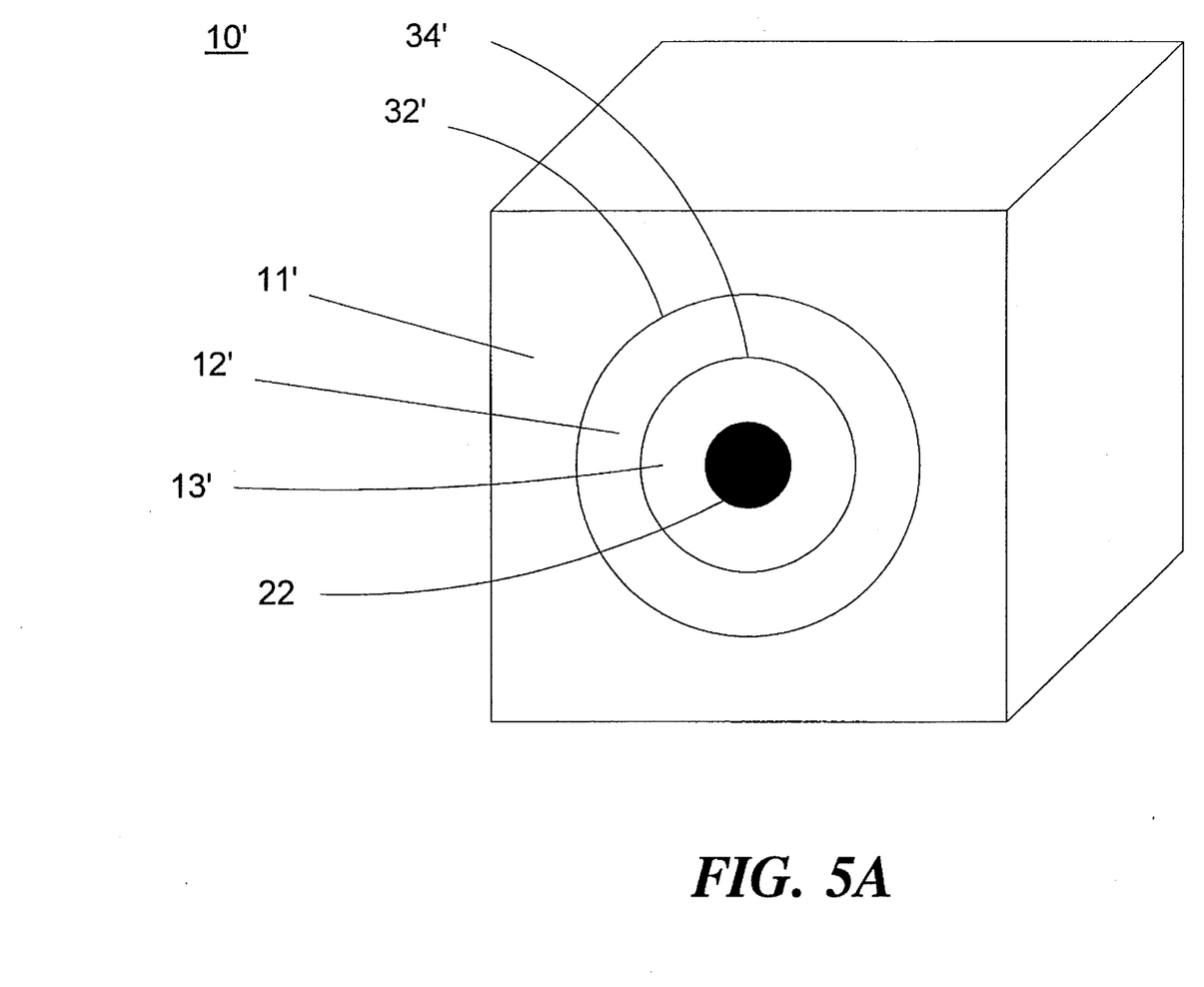
FIG. 5A is a diagrammatic view of another alternative phantom assembly in accordance with the present invention.

FIG. 5A shows the phantom of FIG. 1 arranged as set of concentric hollow cylinders 12', 13' inserted into a base 11' having a cylindrical recess. In this Embodiment, curved sections of rasiochromic film can be placed in the spaces 32', 34' between adjacent cylinders. Opening 22 is provided for insertion of the X-ray probe (not shown). Similarly, the subsection of the phantom of FIG. 5 can be constructed in this fashion as well. In addition, it is not necessary that the cylinder be circular, the cylinder can have any polygonal cross-section with flat pieces of film held in the spaces on each side.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A phantom assembly comprising:
a tissue equivalent volume matrix bounded by a peripheral surface and having a radiation transmission characteristic substantially the same as a living tissue matrix, said volume matrix including at least two locations where radiation sensitive film can be inserted, exposed and then removed for imaging,
wherein two of said locations are each substantially planar and wherein said two locations are mutually non-parallel.

2. A phantom assembly according to claim 1, wherein said volume matrix includes at least three locations where radiation sensitive film can be inserted, exposed and then removed for imaging, wherein said three locations are each substantially planar and wherein said three locations are mutually orthogonal.

3. A phantom assembly according to claim 2, wherein said three locations intersect at a common point.

4. A phantom assembly according claim 1 wherein at least one of said locations extends from said peripheral surface into said volume matrix.

5. A phantom assembly according claim 2 wherein at least one of said three location extends from said peripheral surface into said volume matrix.

6. A phantom assembly according to claim 1, wherein said volume matrix includes two or more of said locations extending from said peripheral surface into said volume matrix, wherein said two or more of said locations are slits, each substantially planar and wherein said two or more slits are mutually non-parallel.

7. A phantom assembly according to claims 1 or 2 or 3 or 6, wherein said volume matrix is a material from the group consisting of water and living tissue radiologically equivalent materials.

8. A phantom assembly according to claims 1 or 2 or 3 or 6, further comprising one or more radiation sensitive film segments, each of said segments being removably positioned in one of said locations.

9. A phantom assembly according to claim 2, further comprising
at least one piece of radiation sensitive film in at least one of said locations.

10. A phantom assembly according to claim 9, further comprising three pieces of radiation sensitive film arranged in three mutually orthogonal planes,
each of said pieces of radiation sensitive film including at least one notch, and each said at least one notch being mated with a complimentary notch on another of said pieces of radiation sensitive film to form a three dimensional assembly.

11. A phantom assembly comprising:
a tissue equivalent volume matrix bounded by a peripheral surface and having a radiation transmission characteristic substantially the same as a live tissue matrix having similar physical dimensions, said matrix having a principal axis, said matrix comprising:
a plurality of adjacent sections, each pair of said adjacent sections including a pair of co-extensive adjacent surfaces, each pair of co-extensive adjacent surfaces defining a location where radiation sensitive film can be inserted, exposed and removed for imaging and
at least one of said sections includes a portion, having a principal axis and being further divided into a plurality of adjacent subsections, each pair of adjacent subsections including a pair of co-extensive adjacent subsection surfaces, each pair of adjacent subsection surfaces defining a location where radiation sensitive film can be inserted, exposed and removed for imaging.

12. A phantom assembly according to claim 11, wherein:
said adjacent surfaces are substantially transverse to said principal axis of said matrix.

13. A phantom assembly according to claim 11, wherein:
said adjacent subsection surfaces are substantially transverse to said principal axis of said portion and said principal axis of said portion is substantially parallel to said axis of said matrix.

14. A phantom assembly according to claim 11, wherein:
said adjacent subsection surfaces are substantially transverse to said principal axis of said portion and said principal axis of said portion is at an angle to said axis of said matrix.

15. A method of verifying the radiation dose applied by a given treatment, said method of verifying comprising the steps of:

providing a phantom assembly including a tissue equivalent volume matrix having a radiation transmission characteristic substantially the same as a tissue matrix to be treated, said matrix including at least two mutually non-parallel locations where radiation sensitive film can be inserted, exposed and then removed for imaging, inserting at least one piece of radiation sensitive film in at least one of said mutually non-parallel locations, and applying said radiation dosage for said given treatment to said phantom assembly and said radiation sensitive film.

16. A method of verifying the radiation dose applied by a given treatment according to claim 15, further comprising the step of:

scanning said image with a microdensitometer to determine the dosage applied to a specific location on said radiation sensitive film.

17. A phantom assembly comprising:

a tissue equivalent volume matrix bounded by a peripheral surface and having a radiation transmission characteristic substantially the same as a living tissue matrix, said volume matrix including at least two locations extending from said peripheral surface into said volume matrix where radiation sensitive film can be inserted, exposed and then removed for imaging, wherein said at least two locations are slits, each substantially cylindrical and wherein said slits are substantially concentric.

18. A phantom assembly according to claim 17, wherein said volume matrix is a material from the group consisting of water and living tissue radiologically equivalent materials.

19. A phantom assembly according to claim 17, further comprising one or more radiation sensitive film segments, each of said segments being removably positioned in one of said locations.

\* \* \* \* \*